(12) United States Patent
Haerer et al.

(10) Patent No.: US 7,860,208 B2
(45) Date of Patent: Dec. 28, 2010

(54) SCATTER RADIATION CORRECTION IN RADIOGRAPHY AND COMPUTED TOMOGRAPHY EMPLOYING FLAT PANEL DETECTOR

(75) Inventors: Wolfgang Haerer, Erlangen (DE); Ernst-Peter Ruehrnschopf, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 649 days.

(21) Appl. No.: 11/863,495

(22) Filed: Sep. 28, 2007

(65) Prior Publication Data

US 2008/0080663 A1 Apr. 3, 2008

(30) Foreign Application Priority Data

Sep. 29, 2006 (DE) ........................ 10 2006 046 191

(51) Int. Cl.
*A61B 6/03* (2006.01)
(52) U.S. Cl. .......................................................... 378/7
(58) Field of Classification Search ................ 378/7, 378/4, 19, 86, 154, 207; 382/128–131, 260–262, 382/274–275
See application file for complete search history.

(56) References Cited

U.S. PATENT DOCUMENTS

| 4,334,244 | A | 6/1982 | Chan et al. | |
|---|---|---|---|---|
| 6,687,326 | B1 * | 2/2004 | Bechwati et al. | 378/7 |
| 6,925,140 | B2 * | 8/2005 | Bruder | 378/4 |
| 2004/0079232 | A1 | 4/2004 | Groh et al. | |
| 2004/0125917 | A1 * | 7/2004 | Ross et al. | 378/98.8 |
| 2005/0276373 | A1 * | 12/2005 | Ying et al. | 378/7 |
| 2006/0083351 | A1 | 4/2006 | Lamberty et al. | |

FOREIGN PATENT DOCUMENTS

EP 1 035 508 9/2000

OTHER PUBLICATIONS

Scatter Compensation in Digital Radiography-Signal Processing X Theories and Applications, Proceedings of EUSIPCO 2000, Tenth European Signal Processing conference, vol. 1, 2000, pp. 215-128; Vesa Onnia et al.
Bildgebende Systeme für die medizinische Diagnostik—3. Auflage 1995—Herausgeber: Heinz Morneburg; Kapitel 2 "Algorithmen zur Biuldrekonstruktion and Systemtheorie-Kap. 2.1 Einführung in die Bildrekonstruktion", pp. 44 through 47, ISBN: 89578-002-2; Book; 1995; DE.
Peter M. Joseph et al; The Effects of Scatter in X-ray Computed Tomography; Med. Phys.9(4), Jul./Aug. 1982, 464 472; Others; 1982.
Siewerdsen et al; A Simple, Direct Method for C-ray Siewerdsen Scatter Estimation and Correction in Digital Radiography and Cone-Beam CT Siewerdsen et al.; Med. Phys. 33(1), Jan. 2006, 187-197; Others; 2006.
Ning et al—"X-Ray Scatter Suppression Algorithm for Cone Beam Volume CT" Med. Imaging 2002; Proceedings of SPIE vol. 4682 Physics of Medical Imaging Editor(s); Antonuk, Larry #; May 2002 pp. 774-781.
Darboux et al—"Physical Model Based Scatter Correction in Mammography", SPIE vol. 3032, 1997, pp. 405-410.
Dinten et al. "Physical Model Based Restoration of Mammographies" SPIE Conference on Physics Of Medical Imaging, SPIE vol. 3336, 1998, pp. 641-650.
Baydush et al. "Improved Image Quality With Bayesian Image Processing in Digital Mammography" Proc. of SPIE vol. 3979, 2000. pp. 781-786.
Warp et al. "Quantitative Evaluation of Noise Reduction Strategies in Dual-Energy Imaging" Med.Phys. 30(2), Feb. 2003, pp. 190-198.
Siewerdsen et al.—"The Influence of Antiscatter Gridson Soft-Tissue Detectability in Cone-Beam Computed Tomography With Flat-Panel Detectors," Med. Phys. 31 (12). Dec. 2004, pp. 3506-3520.
Zellerhoff et al. Low Contrast 3D-Reconstruction Frm C-arm Data Proceedings of SPIE, Medical Imaging 2005, vol. 5745, pp. 646-655.
Hinshaw et al. "Recent Progress in Noise Reduction and Scatter Correction in Dual-Energy Imaging" SPIE vol. 2432, 1995, pp. 134-142.
Jahne Digitale Bildverarbeitung "Kapitel 10: Mittelwerts and Kanten", pp. 310-364, speziell das Kap. 10.6 "Nichtlineare Mittelung", p. 337-342. 1997.

\* cited by examiner

*Primary Examiner*—Edward J Glick
*Assistant Examiner*—John M Corbett
(74) *Attorney, Agent, or Firm*—Schiff Hardin LLP

(57) ABSTRACT

In a method for correction of scatter radiation errors in radiography and computer tomography, using flat panel detectors, initially an estimation of a scatter radiation distribution $S_{cor}(y,z)$ is undertaken, and a standard correction term $\delta p_{cor}$ is subsequently calculated. Noise filtering of the standard correction term $\delta p_{cor}$ with $F(\delta p_{cor})$ is implemented and subsequently the noise-filtered standard correction term $F(\delta p_{cor})$ is added to the logarithmized measured total projection data $p_s$. The noise filtering can be implemented adaptively dependent on a previously-determined local noise variance. The method can be implemented in a radiography system and/or by a computer for generation and/or processing of projective and/or tomographic exposures, with a memory containing program codes causing the computer in operation to execute the steps of the method.

38 Claims, 4 Drawing Sheets

FIG 1

Prg$_1$-Prg$_n$

SCATTER RADIATION CORRECTION IN RADIOGRAPHY AND COMPUTED TOMOGRAPHY EMPLOYING FLAT PANEL DETECTOR

BACKGROUND OF THE INVENTION

1. Field of the Invention

The invention concerns a method for correction of scatter radiation fields in radiography and computed tomography with flat panel detectors.

2. Description of the Prior Art

From the printed document M. Zellerhoff, B. Scholz, E.-P. Rührnschopf, T. Brunner: "Low Contrast 3D Reconstruction from C-Arm Data", Proceedings of SPIE. Medical Imaging 2005, Vol. 5745, 645-655. It is known that the technology of the flat image detectors (FPD) enables a low-contrast resolution in three-dimensional reconstruction of the tissue density distribution with C-arm computed tomography. Due to the large irradiated patient volume in each projection image, the scatter radiation (which contains only very little image information) represents a significant problem. The effects of the scatter radiation are contrast loss, distortions of the quantitative results (such as cupping and artifacts) and increase of the noise. The use of scattered-ray grids is generally not sufficient. Additional correction methods are therefore required that, on the basis of measurements or computational estimations of the scatter radiation, should compensate its negative effects on the image quality.

In the ideal case the Hounsfield units (HU) and the original contrast between soft tissues are adjusted with such correction methods. Although the quality measure of contrast-to-noise remains, an increase of the image noise normally occurs with the corrections, such that the noise increases in equal measure to the contrast. This effect is stronger the greater the relative scatter radiation proportion S/P (scatter radiation to primary radiation intensity) in the data. This also has an effect in the reconstructed images through strong inhomogeneities of the image noise. These inhomogeneities exhibit both increased noise amplitudes (standard deviation of the pixel noise) and an elongated shape (thus irregular fine stripes) and alignment, particularly in directions in which the x-rays are subject to a strong attenuation, for example the longitudinal axes given elliptical cross-sections, soft tissue between bones, and where the relative scatter radiation proportion S/P is also normally relatively large. This inhomogeneity of the image noise due to scatter radiation corrections is referred to in the printed document P. M. Joseph, R. D. Spital: "The Effects of Scatter in X-Ray Computed Tomography", Med. Phys. 9(4), July/August 1982, 464-472.

For correction of this scatter radiation problem, a simple measurement method was proposed in the printed document J. H. Siewerdsen, M. J. Daily, B. Bakhtiar, D. H. Moseley, S. Richard, H. Keller, D. A. Jaffray "A Simple, Direct Method For X-Ray Scatter Estimation And Correction In Digital Radiography And Cone-Beam Ct", Med. Phys. 33(1), January 2006, 187-197; for estimation of the scatter radiation intensity within the actual measurement field by interpolation of the measurements of the scatter radiation in the collimator shadow outside of the measurement field, for example. However, since the scatter radiation within the measurement field is not measured, this method is only very crude. The problem of the image noise in connection with the correction is not discussed in this document. The concept of purely computational methods for scatter radiation correction in CT with flat panel detectors (cone beam CT) has been discussed in the early stages in the technical literature. A very general computational correction algorithm is described in the aforementioned article by Zellerhoff et al. and other approaches are also cited. Although the essential image quality aspects are addressed, a quantitative image quality analysis is missing.

A problem of these known scatter radiation correction methods lies in that the "signal-to-noise" ratio or the ratio of scatter radiation intensity to primary radiation intensity is worsened by the scatter radiation correction.

SUMMARY OF THE INVENTION

An object of the invention is to provide an improved scatter radiation correction method that worsens the signal-to-noise ratio as little as possible, or not at all.

The following designations are used in the following explanation of background information:

(y,z) coordinates on the detector;

$I_o = I_o(y,z)$ measured unattenuated intensity distribution without subject in radiation path;

$I_t = I_t(y,z)$ measured total intensity distribution with subject (including scatter radiation);

$I_p = I_p(y,z)$ primary intensity distribution with subject in the radiation path (without scatter radiation);

$I_s = I_s(y,z)$ intensity distribution only of the scatter radiation generated by the subject.

In the following, calculations are predominantly made with normalized intensities. Normalization means division by $I_o$. The following designations are introduced for the normalized intensities:

$P = I_p/I_o$ normalized primary radiation distribution (without scatter radiation);

$P_s = I_t/I_o$ normalized total radiation distribution (including scatter radiation);

$S = I_s/I_o$ normalized scatter radiation distribution.

The projection image data are logarithmized in CT. These logarthmized values are called "CT projection values". These are:

Error-free CT projection values:

$$p = -\ln(P) \quad (\#1a);$$

the CT projection values disrupted by scatter radiation are $$p_s = -\ln(P_s) = -\ln(P+S) = p - \ln(1+S/P) \quad (\#1b);$$

the disruption ratio due to scatter radiation is $$\delta p_s = -\ln(1+S/P) \quad (\#1c).$$

The terms contrast, noise transfer and differential CNR given scatter radiation are subsequently explained:

For the following considerations, we require the Taylor formula or, respectively, chain rule of differentiation and the Gaussian error propagation rule. Due to the Taylor formula, $$\Delta f(X) = \frac{\partial f}{\partial X} \Delta X \quad (\#2)$$

applies for the "deterministic" propagation of differential changes $\Delta X$ of expected values $X$ over a differentiable functional map $f$.

The error propagation rule by Gauss for functions $f$ of uncorrelated random variables $X_1, X_2 \ldots$ is:

$$\sigma(f(X_1, X_2, \ldots, X_n)) = \sqrt{\sum_{k=1}^{n} \left(\frac{\partial f}{\partial X_k}\right)^2 \sigma^2(X_k)}. \quad (\#3)$$

The term "differential contrast" is subsequently described. For this a small, infinitesimal signal difference ΔP is assumed and it is asked how this is translated via logarithmization into equation (#1a,b). For this ΔP and Δp are designated as a "differential contrast" given normalized intensity values and logarithmized projection values, respectively. Assuming the differentiability of P, ΔP can also be interpreted as $$\Delta P = \frac{\partial P}{\partial \xi} \Delta \xi$$

with a small spatial displacement Δξ. With scatter radiation, than:

$$\Delta P_s = \Delta(P+S) \approx \Delta P \quad (\#4a).$$

It is assumed that the scatter radiation distribution S(y,z) in the expected value is spatially of very low frequency, meaning that S(y,z) changes only negligibly in comparison to the primary radiation distribution P(y,z); thus |ΔS/ΔP|≈0.

From equation (#2), $\quad (\#4b)$ $$\Delta p = \Delta(-\ln P) = \frac{-\Delta P}{P}$$

follows specifically for f=−ln and X=P.

The signal difference in the logarithmized data is influenced as follows by a scatter radiation background S:

$$\Delta p_s = \Delta(-\ln(P+S)) = \frac{\Delta P + \Delta S}{P+S} \approx \frac{\Delta P}{P+S} = \frac{\Delta p}{1+S/P}. \quad (\#4c)$$

|ΔS/ΔP|≈0 is thereby assumed. For logarithmic projection data, the equation (#4c) indicates that the scatter radiation effects a reduction of the differential contrast by the factor $$\frac{1}{1+S/P}.$$

Under the assumption of the Poisson distribution as a probability distribution, $\sigma(I)=\sqrt{I}$.

With the Gaussian error propagation rule (#3), one obtains $$\sigma\left(\frac{I}{I_0}\right) = \frac{1}{\sqrt{I_0}}\sqrt{\frac{I}{I_0}}\sqrt{1+\frac{I}{I_0}} \approx \frac{1}{\sqrt{I_0}}\sqrt{\frac{I}{I_0}}, \quad (\#5)$$

whereby $I \ll I_o$ and $\sigma(I)=\sqrt{I}$ and $\sigma(I_0)=\sqrt{I_0}$ were considered. I.e., it applies that:

$$\sigma(P) = \frac{1}{\sqrt{I_0}}\sqrt{P} \quad (\#5a)$$

and $$\sigma(P_S) = \sigma(P+S) = \sigma(P)\sqrt{1+S/P}. \quad (\#5b)$$

The noise of the non-logarithmized, normalized intensities is thus increased by a factor of √1+S/P due to the scatter radiation.

The differential contrast-to-noise ratio dCNR, which represents a quotient from a differential signal change and the standard device of the signal noise, is introduced as a reasonable quality measure.

By definition and with equation (#5b), then:

$$dCNR(P) = \left|\frac{\Delta P}{\sigma(P)}\right| \quad (\#6)$$

$$dCNR(P_S) = dCNR(P+S) = \frac{dCNR(P)}{\sqrt{1+S/P}}$$

It is generally true that dCNR is invariant according to magnitude under differentiable (monotonic) signal transformations f, with:

$$dCNR(f(P)) = dCNR(P) \quad (\#7)$$

The proof results by the relationships (#2) and (#3):

In the quotient determination the derivations cancel out in terms of magnitude, since due to the assumption of the monotony of f the derivation is nowhere zero. This in particular applies for the logarithmization f=−ln, whereby given dCNR the algebraic sign reverses. Thus, independent of whether the projection data are logarithmized or not, the scatter radiation causes a reduction of the differential CNR by a factor of $$\frac{dCNR(p_s)}{dCNR(p)} = \frac{dCNR(P_S)}{dCNR(P)} = \frac{1}{1+S/P}. \quad (\#8)$$

In the previous considerations it was assumed that the normalized primary intensity distribution P(y,z) and the scatter intensity distribution S(y,z) are known. In reality only their superimposition, the "total intensity distribution" $P_s(y,z)=P(y,z)+S(y,z)$, is provided by the detector. The scatter radiation distribution S(y,z) thereby represents a disruption. However, the undisturbed primary radiation distribution P(y,z) is sought.

Since the scatter radiation distribution is not exactly known, it must be corrected by an estimation. The estimation can ensue by means of measurements, for example by the beam stop method or by measurement in collimator shadows and interpolation according to the aforementioned Siewardsen et al. article or by computational methods according to the aforementioned article by Zellerhoff et al. Here the designation $S_{cor}(y,z)$ is used for the estimated scatter distribution used for the correction; we write $P_{cor}(Y,z)$ for the primary intensity distribution estimated by means of this correction.

$$P_{cor}(y,z) = P_s(y,z) - S_{cor}(y,z) \quad (\#9a)$$

$$P_{cor}(y,z) = P(y,z) + \epsilon_{cor}(y,z) \quad (\#9b)$$

with the scatter radiation correction error $$\epsilon_{cor}(y,z)=S(y,z)-S_{cor}(y,z) \tag{\#9c}$$

Under the assumption that the correction error is small relative S and P, in the following the effect of the scatter radiation correction on the differential contrast, the noise and the dCNR is examined. For this the logarithmized projection data are also required:

$$p_{cor}=-\ln P_{cor}=-\ln(P_s-S_{cor}) \tag{\#10a}$$

$$p_{cor}=-\ln(P+\epsilon_{cor}) \tag{\#10b}$$

The differential contrast is now reestablished via scatter radiation correction. The interference calculation applied to equation (#10b) provides $$\Delta p_{cor} = \frac{\Delta P + \Delta \varepsilon_{cor}}{P + \varepsilon_{cor}} \approx \frac{\Delta P}{P} \frac{1}{1+\varepsilon_{cor}/P} = \Delta p \frac{1}{1+\varepsilon_{cor}/P}, \tag{\#11}$$

wherein it was utilized that $\epsilon_{cor}$ runs very smoothly and the derivation can locally be set to approximately equal 0. Under the assumption of a negligible correction error $|\epsilon_{cor}|<<|P|$, it thus results that a precise scatter radiation correction of the original differential contrast can be regained, meaning that the scatter radiation-conditional differential contrast loss is compensated by the factor (1+S/P) by the correction through a differential contrast amplification.

The dCNR conservation with scatter radiation correction follows from the invariance relation equation (#7) with $$dCNR(p_{cor})=dCNR(p_s). \tag{\#12}$$

This means that the differential contrast-to-noise ratio (dCNR) remains unchanged by a precise scatter radiation correction.

In spite of this, the increase of the noise due to the scatter radiation correction remains. Namely, the disruption calculation applied to equation (#10a) provides $$\sigma(p_{cor}) = \frac{\sigma(P_s)}{P} \frac{1}{1+\varepsilon_{cor}/P} = \frac{\sigma(P_s)}{P_s} \frac{1+S/P}{1+\varepsilon_{cor}/P} \tag{\#13}$$

$$= \sigma(p_s) \frac{1+S/P}{1+\varepsilon_{cor}/P} \approx \sigma(p_s)(1+S/P).$$

Under the assumption of a negligible correction error $|\epsilon_{cor}|<<|P|$, it accordingly applies that the noise of the logarithmized projection data disrupted by scatter radiation is increased by the factor of (1+S/P) by a precise scatter radiation correction.

This phenomenon leads to a very inhomogeneous amplification of the image noise, primarily in directions with very small values of P (i.e. stronger radiation attenuation). For example, the noise is doubled given a value of S/P=1, a case that occurs not seldom even in spite of scattered-ray grids.

A "standard scatter radiation correction"—based on measurement methods or on computational models—is essentially based on the equation (#10a) and includes the following steps:

estimation of the scatter radiation distribution via measurement or calculation $S_{cor}(y,z)$;
subtraction of the measured "total" distribution $P_s(y,z)$ and logarithmization.

According to equation (#13), the noise increases even when the dCNR is not worsened.

According to the invention, this problem can be circumvented as follows:

The equation (#10a) can be rewritten as follows by factorization of the correction:

$$P_{cor}=P_s-S_{cor}$$

$$P_{cor}=P_s(1-S_{cor}/P_s) \tag{\#14}.$$

Logarithmization then yields:

$$p_{cor}=-\ln P_{cor}=-\ln(P_s)-\ln(1-S_{cor}/P_s)$$

$$p_{cor}=p_s-\ln(1-S_{cor}/P_s)$$

$$p_{cor}=p_s+\delta p_{cor} \tag{\#15}.$$

The standard scatter radiation correction term is thereby generally defined via $$\delta p_{cor}=p_{cor}-p_s \tag{\#16}.$$

Equation (#16) applies generally, nor only for subtractive corrections as in equation (#15) but rather also for multiplicative corrections as mentioned, for example, in the aforementioned article by Zellerhoff et al.

The function $S_{cor}(y,z)$ in equation (#14) is very smooth and practically without noise. In contrast to this, the standard correction term $\delta p_{cor}(y,z)$ for the logarithmic data is no longer smooth, but rather is highly modulated due to the division by $P_s(y,z)$ and is therefore also noisy. The noise is strongly correlated with that of $P_s$. In fact, the possibility of the contrast restoration is based on the dependency on $P_s$, but unfortunately with the side effect of an increase of the noise.

The basis of the invention is based on first applying an optimally contrast-conserving noise filtering solely to the scatter radiation correction term $\delta p_{cor}$ and only then adding the noise-filtering correction term to the uncorrected data $p_s$.

If the noise filtering is symbolized with an operator F, equation (#15) is replaced by $$p_{cor,F}=p_s+F(\delta p_{cor}) \tag{\#17a}.$$

In general the noise filtering is non-linear and two-dimensional, but can also be selected as only one-dimensional in the image line direction, for example. Examples are one-dimensional or two-dimensional median filtering. Median filtering is the simplest example for edge-conserving and noise-reducing filtering. In contrast to the "standard scatter radiation correction", this basic method includes the following steps:

estimation of the scatter radiation distribution (via measurement or calculation) $S_{cor}(y,z)$;
calculation of the standard correction term $\delta p_{cor}$ according to equation (#15) or, respectively, (#16);
noise filtering of the standard correction term: $F(\delta p_{cor})$
addition of the noise-filtered standard correction term $F(\delta p_{cor})$ to the (logarithmized) measured "total" projection data $p_s$.

This is the simplest variant of the inventive radiation correction. According to an embodiment of the method, an adaptive noise filtering of the correction term can also be implemented, whereby now a noise-adaptive and improve contrast-conserving noise filtering is applied. If the adaptive noise filtering is symbolized with an operator Φ, equation (#15) is then replaced by $$p_{cor,\Phi}=p_s+\Phi(\delta p_{cor}) \tag{\#17b}.$$

As used herein, noise-adaptive means that the noise should be more strongly filtered the greater the standard deviation, such that the standard deviation of the noise is "homogenized" after the filtering. This homogenization of the noise in the scatter radiation correction term in the projection data will likewise become noticeable in a homogenization of the noise in the reconstructed CT images.

Simple examples for adaptive filters are found in the standard literature about image processing, for example Bernd Jähne: "Digitale Bildverarbeitung", Springer-Verlag, 1997, 4th edition, noise-dependent normalized convolution, controllable filters with filter masks dependent on the local image structure, median filters and general smoothing filters with noise-dependent mask size.

In order to not alter the local image structure by the filtering, in particular to optimally not smooth edges, for example, a prior image analysis by means of edge detection and/or segmentation is appropriate. Different image regions can thereby be filtered differently, i.e. adaptively. For example, edges can be filtered only in the longitudinal direction and not in the transverse direction. Median filters already have the advantageous property that they largely retain edges, but their noise reduction effect given mask enlargement is less than given linear averaging filters.

According to the invention, it is particularly advantageous to implement the image analysis (thus the edge detection and/or segmentation) in the uncorrected image pS since the image structures there are generally more clearly recognizable than in the correction term.

The standard deviations are then to be estimated from the uncorrected projection image (possibly in the segmented image regions in the event that a segmentation was implemented) in order to adaptively determined, dependent on said standard deviations, the size of the local noise filter mask for noise filtering in a pixel environment.

From the equations (#5a-b) and $P_s = e^{-p_s}$ it follows that:

$$\sigma(p_s) = \sqrt{\frac{e^{p_s}}{I_0}} \quad (\#18)$$

This quantity can be calculated for each pixel from the uncorrected projection image $p_s$.

The image noise is increased by the scatter radiation correction according to equation (#13). In our estimation this can be taken into account via multiplication with the factor (S/P) in equation (#18). An estimation of (S/P) with equation (#9a) yields $S_{cor}/P_{cor} = S_{cor}/(P_s - S_{cor})$.

The following quantity $$(S/P) * \sigma(p_s) * \sqrt{I_0} \approx \sqrt{e^{p_s}} \frac{S_{cor}}{P_{cor}} \quad (\#19)$$

is designated as a "noise growth term".

When one assumes that the pixel noise is statistically uncorrelated, the standard deviation can then be reduced via averaging across N*N pixels proportional to the factor 1/N. A measure for adaptive determination of the mask size of averaging filters for noise reduction results in this manner.

The absolute values of the standard deviation in equation (#18) are not necessary, meaning that the unattenuated intensity value $I_0$ is also not necessary. Since only the inhomogeneity growth of the noise should be reduced by the scatter radiation correction (that is primarily determined by large values of the "noise growth term"), it is sufficient to limit the adaptive noise filtering to regions with relatively large values of the "noise growth term" of equation (#19). Assuming average values of the "noise growth term", a noise filtering is made only across a normal mask size N0*N0; however, if values of the term (#19) greater by, for example, a factor of 3 occur in an image region, the normal averaging mask in this region must then be enlarged to N*N with N=3*N0. Depending on the case—for example along edges, dependent on the segmentation—rectangular averaging masks instead of quadratic can also occur.

The inventive processing chain accordingly includes the following steps:
estimation of the scatter radiation distribution (via measurement or calculation) $S_{cor}(y,z)$,
calculation of the scatter radiation correction term $\delta p_{cor}$ according to equation (#15),
image analysis via edge detection and/or segmentation of the uncorrected projection image $p_s$,
determination of the local noise variance,
adaptive determination of the local noise filter mask size,
adaptive noise filtering of the standard correction term: $\Phi(\delta p_{cor})$,
addition of the noise-filtered correction term $\Phi(\delta p_{cor})$ to the (logarithmized) measured "total" projection data $p_s$.

The described image quality analysis and the inventive solution suggestion have the following advantages with regard to the elimination and adaptive noise filtering of the scatter radiation correction term:
the inhomogeneity of the image noise, represented as irregular lines and elongated "noise worms" instead of isotropic "salt and pepper", is homogenized by the adaptive noise filtering,
the specific noise filtering of the scatter radiation correction term considerably reduces the increase of the noise via the scatter radiation correction,
the contrast-restoring effect of the scatter radiation correction can largely be retained,
the differential contrast-to-noise ratio dCNR in the end effect is thereby distinctly improved relative to the standard correction without separation and noise filtering and the ideal case without scatter radiation is approximated,
the uncorrected portion $p_s$ of the data was initially left unchanged in order to assess the quality improvement independent of downstream image post-processing algorithms; naturally, such known downstream image post-processing algorithms that are used customarily or as needed can also furthermore be applied after the inventive correction (then to $p_{cor,\Phi}$), and
the solution suggestion is applicable given scatter radiation correction methods based both on measurements and computation models.

Corresponding to the fundamentals of the invention described above, the inventive method in different variants is as follows:

a) Method for correction of scatter radiation errors in radiography and computer tomography, respectively with flat panel detectors, with the following method steps:
estimation of a scatter radiation distribution $S_{cor}(y,z)$,
calculation of a standard correction term $\delta p_{cor}$,
noise filtering of the standard correction term $\delta p_{cor}$ with $F(\delta p_{cor})$,
addition of the noise-filtered standard correction term $F(\delta p_{cor})$ to the logarithmized, measured total projection data $p_s$.

b) Method for correction of scatter radiation errors in radiography and computer tomography, respectively with flat panel detectors, with the following method steps:

estimation of a scatter radiation distribution $S_{cor}(y,z)$, calculation of a standard correction term $\delta p_{cor}$, determination of a local noise variance, adaptive determination of a local noise filter mask size, adaptive noise filtering of the standard correction term $\delta p_{cor}$ with $\Phi(\delta p_{cor})$, addition of the noise-filtered standard correction term $\Phi(\delta p_{cor})$ to the logarithmized, measured total projection data $p_s$.

c) Method for correction of scatter radiation errors in radiography and computer tomography, respectively with flat panel detectors, with the following method steps:

estimation of a scatter radiation distribution $S_{cor}(y,z)$, calculation of a standard correction term $\delta p_{cor}$, determination of a local noise variance, determination of a local noise growth term, whereby an adaptive noise correction is implemented as of a predetermined size of the noise growth term, with:

an adaptive determination of a local noise filter mask size, an adaptive noise filtering of the standard correction term $\delta p_{cor}$ with $\Phi(\delta p_{cor})$, an addition of the noise-filtered standard correction term $\Phi(\delta p_{cor})$ to the logarithmized, measured total projection data $p_s$, and a non-adaptive noise correction ensues when the noise growth term has not reached the predetermined size of the noise growth term, with:

a noise filtering of the standard correction term $\delta p_{cor}$ with $F(\delta p_{cor})$ and addition of the noise-filtered standard correction term $F(\delta p_{cor})$ to the logarithmized, measured total projection data $p_s$.

This variant c) represents a combination of the method variants a) and b), with the application of the respective method variants being triggered by the size of the noise growth term.

d) Method for correction of scatter radiation errors in radiography and computer tomography, respectively with flat panel detectors, with the following method steps:

estimation of a scatter radiation distribution $S_{cor}(y,z)$, calculation of a standard correction term $\delta p_{cor}$, segmentation of an uncorrected projection image $p_s$, determination of a local noise variance, segment-dependent determination of a local noise filter mask size, segment-dependent noise filtering of the standard correction term $\delta p_{cor}$ with $\Phi(\delta p_{cor})$, addition of the noise-filtered correction term $\Phi(\delta p_{cor})$ to the logarithmized, measured total projection data $p_s$.

Finally, in the method variant d) the method according to variant b) is modified to the extent that the adaptive noise filtering is applied to a previously-segmented projection image. A segment-dependent filtering can hereby now be implemented by, for example, implementing a direction-oriented filtering occurs at edges detected via the segmentation and/or noise filterings of different strength are implemented in regions of bone and tissue. In addition, the segmented noise-filtering can also be executed at least partially adaptively dependent on local properties.

In the aforementioned methods, the adaptive noise filtering is preferably implemented dependent on the previously-determined local noise variance.

In all variants cited above, the calculation of the standard correction term $\delta p_{cor}$ can be implemented with the following equation:

$$\delta p_{cor} = -\ln(1 - S_{cor}/P_s),$$

wherein $S_{cor}/P_s$ corresponds to the normalized total intensity distribution including scatter radiation.

Alternatively, the calculation of the standard correction term $\delta p_{cor}$ can also be implemented according to the following equation:

$$\delta p_{cor} = p_{cor} - p_s,$$

wherein $p_{cor} = -\ln(P_s) - \ln(1 - S_{cor}/P_s)$, $p_s$ corresponds to the logarithmized total projection data and $P_s$ corresponds to the normalized total intensity distribution including scatter radiation.

The estimation of the scatter radiation distribution $S_{cor}(y,z)$ can be executed via measurement on the one hand, by calculation on the other hand.

The scope of the invention encompasses not only the method described above but also projective and tomographical radiography systems that use a computer with stored programs, wherein at least one program executes the method illustrated above.

Moreover, the invention also encompassed dedicated computers in which an image processing of projective and tomographic exposures occurs, wherein the computer has a memory with program code which in operation executes the method described above.

DESCRIPTION OF THE PREFERRED EMBODIMENTS

Figure 1:
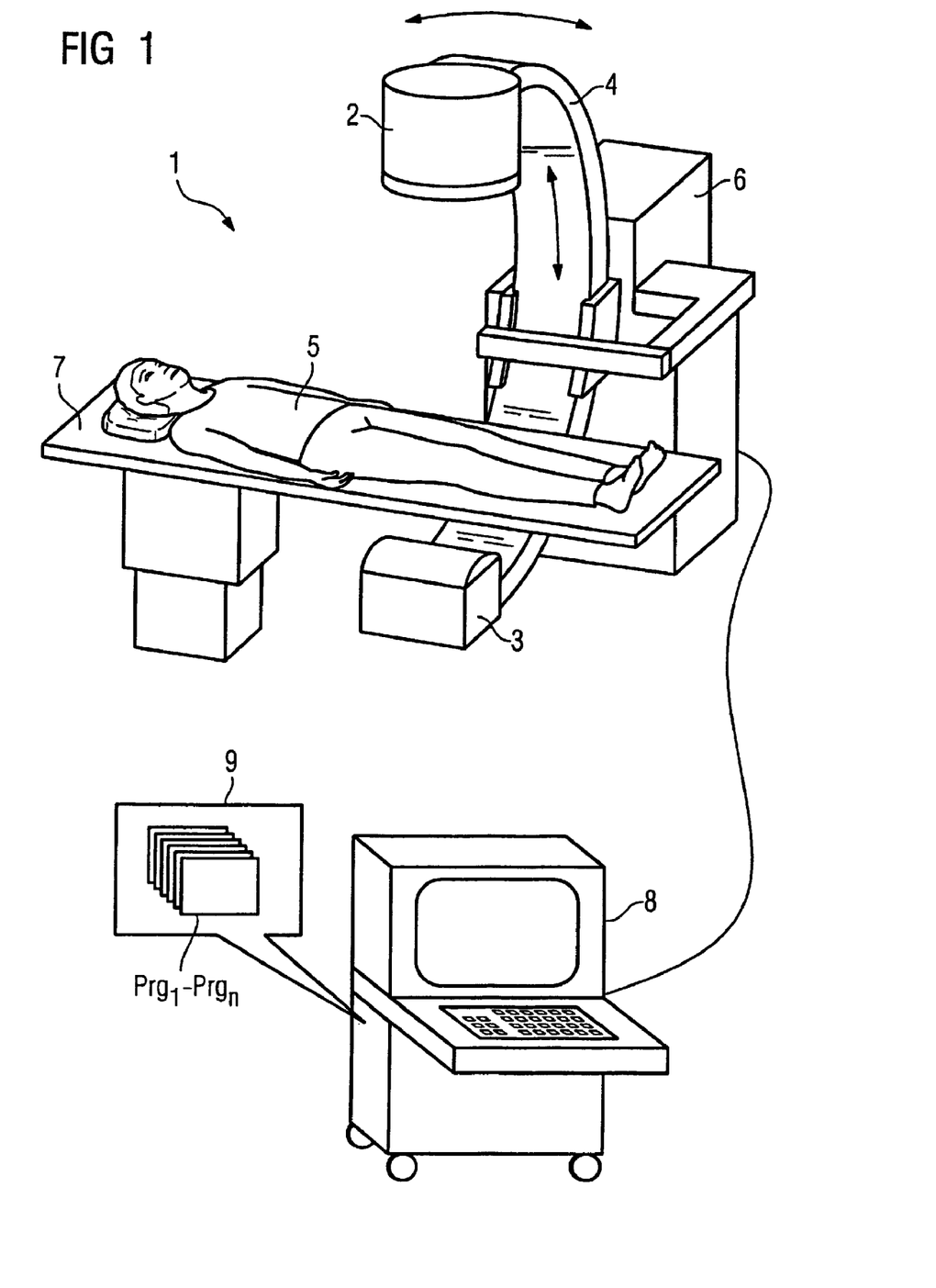
FIG. 1 illustrates a C-arm system with a flat panel detector and a control and computation system for image preparation.

FIG. 1 illustrates a C-arm system 1 with which projective and tomographical x-ray exposures can be generated. It has a C-arm 4 attached to a housing 6, the C-arm 4 being movable around a patient 5. An x-ray tube 2 is arranged at one end of the C-arm 4 and a flat detector (FPD) 3 is arranged at the other end of the C-arm 4. The patient 5 is located on a movable patient bed 7, such that the patient 5 and a region thereof to be examined can be moved into the measurement field between the x-ray tube 2 and the detector 3 of the C-arm system 1. A control and computation unit 8 with a memory 9 in which corresponding control and image processing programs $Prg_1$-$Prg_n$ can run as needed is used for control of the system 1. Program code for implementation of the inventive method is also stored in the memory 9, such that the scatter radiation occurring in the system can be corrected.

The following illustrations of FIG. 2-17 are based on simulation calculations, whereby a simulation subject (phantom)—a homogeneous plate made from material resembling water (for example water or Plexiglass)—with a linear attenuation coefficient $\mu=0.25$/cm and a layer thickness D=20 cm (corresponding to $p=\mu D=5$) is used. Arranged in the middle of the plate is a small square made from the same material with only 0.2 cm thickness in order to simulate a contrast jump by (relatively) 1/1000. It therewith results: $p+\Delta p=5.005$.

Figure 3:
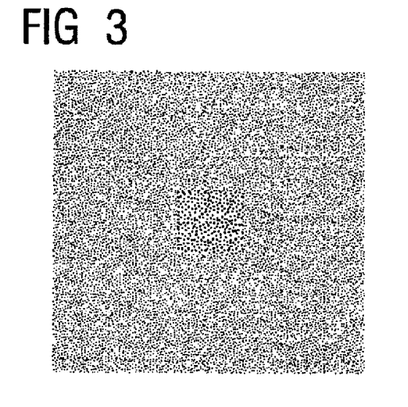
FIG. 3 shows a logarithmic projection image.

The projection image is shown in FIG. 3.

The image size amounts to 1000×1000 pixels and the low-contrast square is the inner 200×200 pixels.

Simplified, it is assumed that effectively 400,000 x-ray quanta are completely absorbed on average per pixel given unattenuated radiation without phantom and are converted into a measurement signal, with the physical detection process in detail being of no importance.

The radiation attenuation in the plate reduces the number of the registered quanta by a factor of exp(−5) to 2695 outside of the low contrast square, or by exp(−5.005), to 2682 quanta inside of the square. The intensity image without noise is reproduced in FIG. 5.

The noise conforms to the Poisson statistic, with the standard deviation corresponding to the square root of the average value. In the simulation a random generator was used for uncorrelated, normally-distributed random numbers. Given the relatively large average values the Poisson distribution can be approximated by normal distribution.

For demonstration of the effect of a scatter radiation intensity of the same strength as the primary intensity, a scatter radiation background intensity corresponding to 2682 pixels is assumed that additively superimposes on average. The standard deviation of the noise thereby increases by a factor of $\sqrt{2}$.

Figure 5:
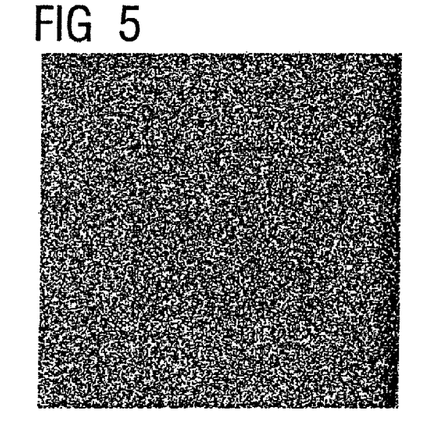
FIG. 5 shows an intensity image with summed scatter radiation.
Figure 6:
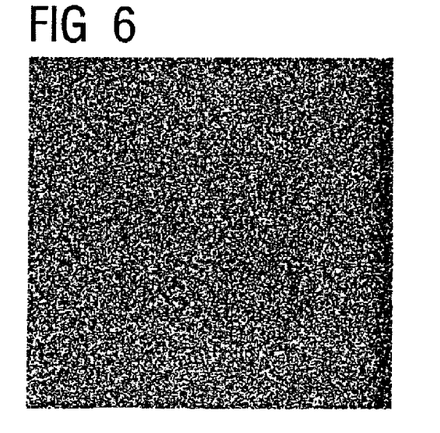
FIG. 6 shows an intensity image with scatter radiation correction.

The zoomed intensity images without and with scatter radiation are shown with noise in FIGS. 5 and 6.

Figure 2:
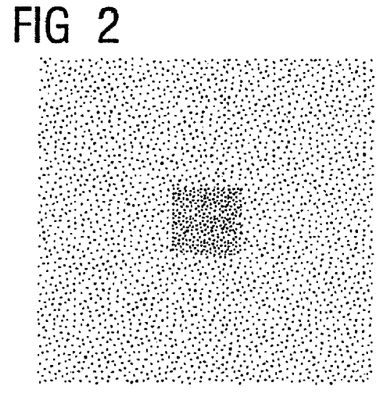
FIG. 2: shows an intensity image I(y,z).

FIG. 2 therewith shows an intensity image with an expected value, without noise and without scatter radiation after the transmission through the simulated phantom. FIG. 6 shows a projection image after normalization and logarithmization.

In the following images the region with the weak contrast square is shown zoomed.

Figure 4:
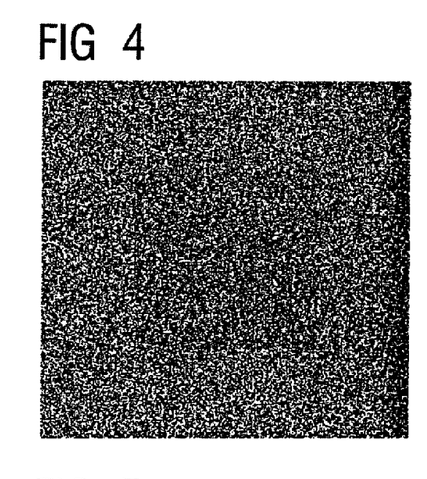
FIG. 4 shows an intensity image without scatter radiation.

FIGS. 4 through 5 and 7 through 9 are intensity images. FIG. 4 shows the intensity image without scatter radiation; in FIG. 5 a superimposition of a constant scatter radiation background exists, whereby the grey value window was correspondingly shifted such that the average grey value remains the same. The increase of the noise due to the scatter radiation and the thereby poorer distinguishability of the square is noticeable here.

Figure 8:
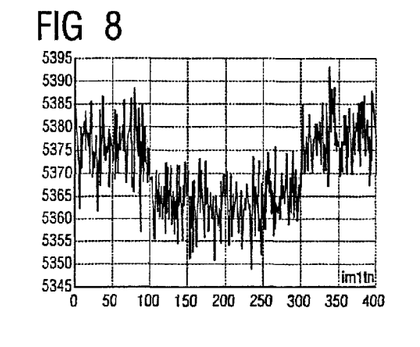
FIG. 8 is a profile plot of the intensity image from FIG. 5.
Figure 9:
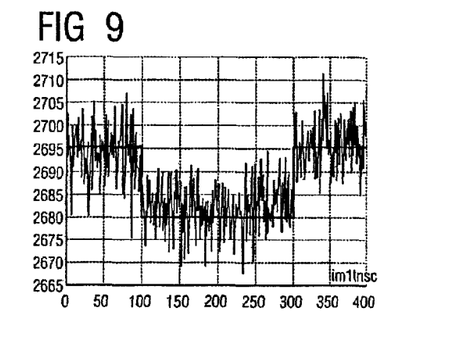
FIG. 9 is a profile plot of the intensity image from FIG. 6.

FIG. 9 shows a simulated scatter radiation correction via digital subtraction of the constant expected value S of the scatter radiation background. The grey value window was not selected identically as in FIG. 7. The image impression is identical with that of FIG. 8.

Figure 7:
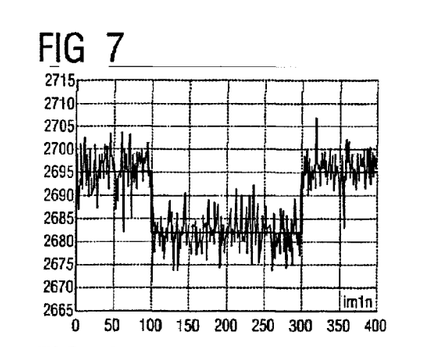
FIG. 7 is a profile plot of the intensity image of FIG. 4.

FIGS. 7 through 9 are profile plots through the middle image lines in the corresponding images in FIGS. 4 through 6.

Figure 10:
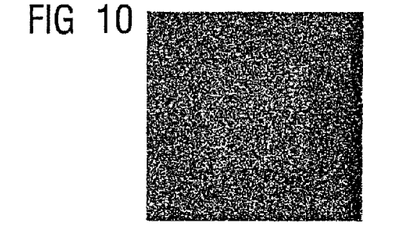
FIG. 10 shows a logarithmic projection image without scatter radiation.
Figure 13:
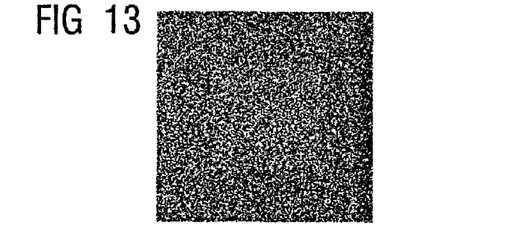
FIG. 13 shows a logarithmic projection image with scatter radiation correction according to the prior art.
Figure 14:
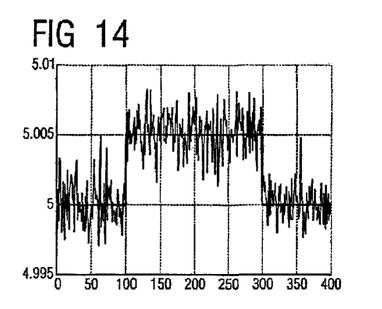
FIG. 14 is a profile plot of the logarithmic projection image from FIG. 10.
Figure 15:
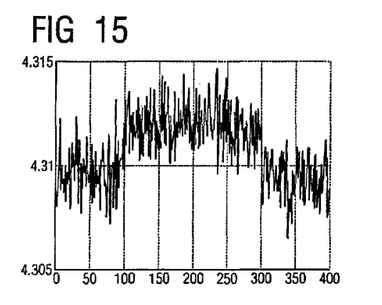
FIG. 15 is a profile plot of the logarithmic projection image from FIG. 11.
Figure 16:
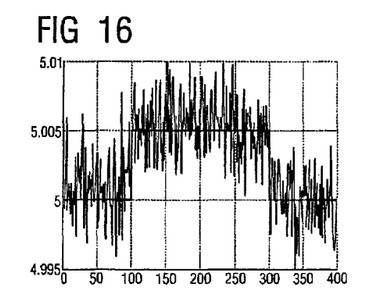
FIG. 16 is a profile plot of the logarithmic projection image from FIG. 12.

Logarithmic projection data and the effect of the method proposed by us are shown as of FIG. 10. FIGS. 12 through 14 are the images of the normalized and logarithmized projection data corresponding to the intensity images from FIGS. 4 through 6, whereby FIG. 10 shows the logarithmic projection data without scatter radiation; a superimposition of the scatter radiation background is shown in FIG. 12. Here the grey value window is correspondingly shifted while retaining the window width, such that the average grey value remains the same. The reduction of the contrast of the inner square is noticeable. Shown in FIG. 12 is the image of FIG. 11 after a standard scatter radiation correction according to the prior art, whereby the grey value window is identical to that in FIG. 10. The increase of the noise relative to FIG. 10 is noticeable.

The result of a noise-filtered scatter radiation correction according to the inventive suggestion follows in closing in FIG. 13. Here a 2-dimensional median filtering with 3×3 mask size was used as a noise filtering. The noise reduction relative to FIG. 12 clearly recognizable, but the remaining image noise appears to be somewhat more coarse-grained than the original image noise in FIG. 10.

Figure 17:
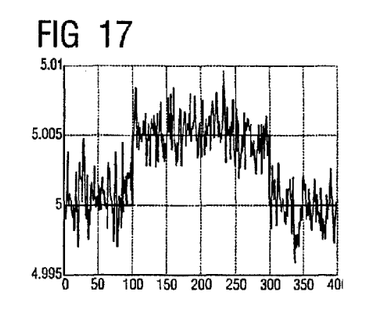
FIG. 17 is a profile plot of the logarithmic projection image from FIG. 13.

FIGS. 14 through 17 again pose profile plots through the middle image lines in the corresponding images in FIGS. 10 through 13. From these plots it can already be qualitatively recognized that the signal difference is "compressed" by approximately half by the scatter radiation (see FIG. 15 versus FIG. 14), the noise increases due to the standard correction in FIG. 16 and, as can be recognized from FIG. 17, is "damped" again to approximately the original strength by the inventive noise-filtered correction.

Figure 11:
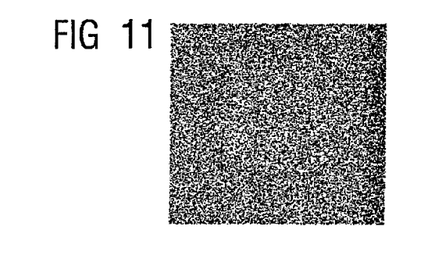
FIG. 11 shows a logarithmic projection image with summed scatter radiation.
Figure 12:
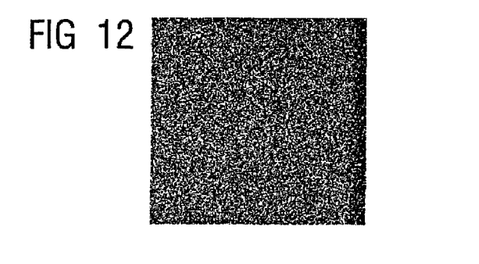
FIG. 12 shows a logarithmic projection image with noise-filtered scatter radiation correction with a 2-dimensional median filtering.
Figure 18:
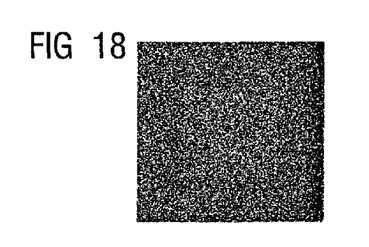
FIG. 18 shows a logarithmic projection image without scatter radiation.
Figure 19:
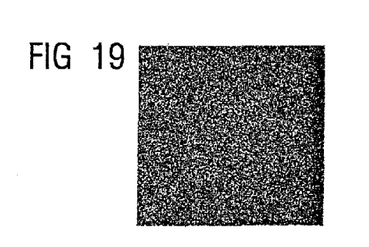
FIG. 19 shows a logarithmic projection image with summed scatter radiation.
Figure 20:
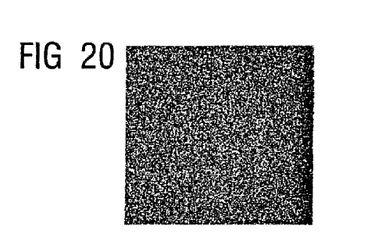
FIG. 20 shows a logarithmic projection image with noise-filtered scatter radiation correction with a 1-dimensional median filtering.
Figure 21:
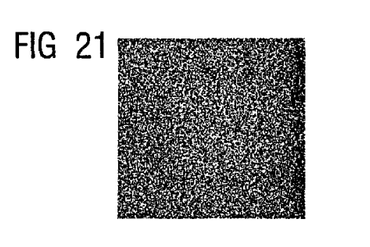
FIG. 21 shows a logarithmic projection image with scatter radiation correction according to the prior art.

FIGS. 18 through 20 correspond to FIGS. 10 through 12 and were presented again for better comparison possibility. In FIG. 21 the correction term was subjected to a line-by-line 1-dimensional median filtering with a mask length of 3 pixels. Relative to FIG. 13, the noise impression is more finely grained and is again similar to as in FIG. 10 or, respectively, FIG. 18.

For the purpose of a statistical evaluation, 10 simulation passes were run through and images corresponding to FIGS. 18 through 20 were respectively generated. The images of the various simulation passes (samples) are statistically independent. For the evaluation average values were respectively established over the 10 simulations.

Designated in the following table are:

"Signal background"=average value across 200×200 pixels outside of the square and averaged over 10 images;

"Signal difference"=ditto within the low-contrast square, minus signal background;

"Noise"=standard deviation of the pixel noise;

dCNR=signal difference/noise.

| | Signal background abs \| (rel) | Signal difference abs \| (rel) | Noise abs \| (rel) | dCNR abs \| (rel) |
|---|---|---|---|---|
| a) without scatter radiation | 5.00 (1.0) | 0.00499 (1.0) | 0.0194 (1.0) | 0.258 (1.0) |
| b) with scatter radiation | 4.31 (0.86) | 0.00243 (0.49) | 0.0137 (0.71) | 0.178 (0.69) |
| c) standard correction | 5.00 (1.0) | 0.00485 (0.97) | 0.0274 (1.41) | 0.177 (0.69) |
| d) noise-filtered correlation with 1-dim. Median filtering | 5.00 (1.0) | 0.00485 (0.97) | 0.0199 (1.41) | 0.244 (0.95) |

"Signal background" = average value across 200 × 200 pixels outside of the square and average over 10 images;
"Signal difference" = ditto within the low-contrast square, minus signal background;
"Noise" = standard deviation of the pixel noise;
dCNR = signal differnce/noise.

The statistical precision of the evaluation of the sample lies at approximately 3%. Again one clearly recognizes the theoretical relations to be expected in the signal difference, namely a loss by half due to scatter radiation or, respectively, given noise (factor $\sqrt{2}$) or, respectively, given dCNR (factor $1/\sqrt{2}$).

The right column shows that, with the proposed method, the ideal case without scatter radiation approaches approximately 95% in relation to the dCNR (=differential contrast-to-noise ratio)

In summary, the invention provides a method for correction of scatter radiation errors in radiography and computer tomography (with flat panel detectors), wherein initially a computational or measured estimation of a scatter radiation distribution occurs; a standard correction term is subsequently calculated; a noise filtering of the standard correction term is implemented; and an addition of the noise-filtered standard correction term to the logarithmized, measured total projection data finally occurs. The noise filtering can also be implemented adaptively dependent on a previously-determined local noise variance. Furthermore, a combination of simple and adaptive noise filtering, advantageously with a decision for the linear or adaptive filtering dependent on a previously-determined noise growth term, can also be implemented across the detector data. Alternatively, the possibility also exists to initially implement a segmentation of the (advantageously unprocessed) projection data and to execute the noise filtering adaptively dependent on the segment.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for correction of scatter radiation errors in radiography and computed tomography using flat panel detectors comprising the steps of:
   estimating a scatter radiation distribution $S_{cor}(y,z)$, where (y,z) represent the coordinates on the detector;
   automatically electronically calculating a standard correction term $\delta p_{cor}$, based on the estimated scatter radiation distribution $S_{cor}(y,z)$;
   automatically electronically determining a local noise variance;
   automatically electronically adaptively determining a local noise filter mask size;
   automatically electronically adaptively noise filtering the standard correction term $\delta p_{cor}$ with $\phi(\delta_{cor})$; and
   automatically electronically adding the noise-filtered correction term $\phi(\delta p_{cor})$ to the logarithmized measured total projection data $p_s$.

2. A method according to claim 1 comprising calculating the standard correction term $\delta p_{cor}$ with the equation:

$\delta p_{cor} = -\ln(1 - S_{cor}/P_s)$, wherein $P_s$ is the normalized total intensity distribution including scatter radiation.

3. A method according to claim 1 comprising calculating the standard correction term $\delta p_{cor}$ with the equation:

$\delta p_{cor} = p_{cor} - p_s$, wherein $p_{cor} = -\ln(P_s) - \ln(1 - S_{cor}/P_s)$, $p_s$ is the logarithmized total projection data, and $P_s$ is the normalized total intensity distribution including scatter radiation.

4. A method according to claim 1 comprising estimating the scatter radiation distribution $S_{cor}(y,z)$ by measurement thereof.

5. A method according to claim 1 comprising the estimating the scatter radiation distribution $S_{cor}(y,z)$ by calculation thereof.

6. A method according to claim 1 comprising implementing the adaptive noise filtering dependent on a previously determined local noise variance.

7. A method for correction of scatter radiation errors in radiography and computed tomography using flat panel detectors, comprising the steps of:
   estimating a scatter radiation distribution $S_{cor}(y,z)$, where (y,z) represent the coordinates on the detector;
   automatically electronically calculating a standard correction term $\delta p_{cor}$, based on the estimated scatter radiation distribution $S_{cor}(y,z)$;
   automatically electronically determining a local noise variance;
   automatically electronically determining a local noise growth term;
   when said growth term reaches a predetermines size automatically electronically implementing an adaptive noise correction by adaptively determining a local noise filter mask size, adaptively noise filtering the standard correction term $\delta p_{cor}$ with $\phi(\delta p_{cor})$, and adding the noise-filtered standard correction term $\phi(\delta p_{cor})$ to the logarithmized, measured total projection data $p_s$; and
   automatically electronically implementing a non-adaptive noise correction when the noise growth term has not reached said predetermined size, by noise filtering the standard correction term $\delta p_{cor}$ with $F(\delta p_{cor})$ $F(\delta p_{cor})$, and adding the noise-filtered standard correction term $F(\delta p_{cor})$ to the logarithmized, measured total projection data $p_s$.

8. A method according to claim 7 comprising calculating the noise growth term with the equation $(S/P) * \sigma(p_s) * \sqrt{I_0}$, wherein S is the normalized scatter radiation distribution, P is the normalized primary radiation distribution, $\sigma(p_s)$ is the interference ratio due to scatter radiation and $I_0$ is the unattenuated intensity distribution without a subject in the beam path of radiation in which said flat panel is disposed.

9. A method according to claim 7 comprising calculating the noise growth term with the equation $$\sqrt{e^{p_s}} \frac{S_{cor}}{P_{cor}},$$

wherein $S_{cor}$ is the estimated scatter radiation used for the correction, $P_{cor}$ is the estimated primary intensity distribution corrected with $S_{cor}$, and $P_s$ is the total intensity distribution.

10. A method according to claim 7 comprising calculating the standard correction term $\delta p_{cor}$ with the equation:

$$\delta p_{cor} = -\ln(1 - S_{cor}/P_s),$$

wherein $P_s$ is the normalized total intensity distribution including scatter radiation.

11. A method according to claim 7 comprising calculating the standard correction term $\delta p_{cor}$ with the equation:

$$\delta p_{cor} = p_{cor} - p_s,$$

wherein $p_{cor} = -\ln(P_s) - \ln(1 - S_{cor}/P_s)$, $p_s$ is the logarithmized total projection data, and $P_s$ is the normalized total intensity distribution including scatter radiation.

12. A method according to claim 7 comprising estimating the scatter radiation distribution $S_{cor}(y,z)$ by measurement thereof.

13. A method according to claim 7 comprising estimating the scatter radiation distribution $S_{cor}(y,z)$ by measurement thereof.

14. A method according to claim 7 comprising the estimating the scatter radiation distribution $S_{cor}(y,z)$ by calculation thereof.

15. A method for correction of scatter radiation errors in radiography and computed tomography using flat panel detectors, comprising the steps of:
    estimating a scatter radiation distribution $S_{cor}(y,z)$, where (y,z) represent the coordinates on the detector;
    automatically electronically calculating a standard correction term $\delta p_{cor}$ based on the estimated scatter radiation distribution $S_{cor}(y,z)$;
    automatically electronically segmenting an uncorrected projection image;
    automatically electronically determining a local noise variance;
    automatically electronically implementing a segment-dependent determination of a local noise filter mask size;
    automatically electronically implementing segment-dependent noise filtering of the standard correction term $\delta p_{cor}$ with $\phi(\delta p_{cor})$; and
    automatically electronically adding the noise-filtered correction term $\phi(\delta p_{cor})$ to the logarithmized, measured total projection data $p_s$.

16. A method according to claim 15 comprising implementing segment-dependent noise filtering at least partially as an adaptive noise variance-dependent noise filtering.

17. A method according to claim 15 comprising calculating the standard correction term $\delta p_{cor}$ with the equation:

$$\delta p_{cor} = -\ln(1 S_{cor}/P_s),$$

wherein $P_s$ is the normalized total intensity distribution including scatter radiation.

18. A method according to claim 15 comprising calculating the standard correction term $\delta p_{cor}$ with the equation:

$$\delta p_{cor} = p_{cor} - p_s,$$

wherein $p_{cor} = -\ln(P_s) - \ln(1 - S_{cor}/P_s)$, $p_s$ is the logarithmized total projection data, and $P_s$ is the normalized total intensity distribution including scatter radiation.

19. A method according to claim 15 comprising estimating the scatter radiation distribution $S_{cor}(y,z)$ by measurement thereof.

20. A method according to claim 15 comprising estimating the scatter radiation distribution $S_{cor}(y,z)$ by measurement thereof.

21. A radiography system comprising:
    an x-ray imaging system comprising an x-ray source that emits a radiation beam onto a flat panel radiation detector, to acquire tomographic data from a subject in a scan having a scatter radiation distribution $S_{cor}(y,z)$, where (y,z) represent the coordinates on the detector associated therewith; and
    an imaging computer configured to generate an image from the tomographic data and automatically correct scatter radiation errors by estimating said scatter radiation distribution $S_{cor}(y,z)$, automatically calculating a standard correction term $\delta p_{cor}$ based on the estimated scatter radiation distribution $S_{cor}(y,z)$, automatically adaptively determining a local noise filter mask size, automatically adaptively noise filtering the standard correction term $\delta p_{cor}$ with $\phi(\delta p_{cor})$, and automatically electronically adding the noise-filtered correction term $\phi(\delta p_{cor})$ to the logarithmized measured total projection data $p_s$.

22. A radiographic system according to claim 21 wherein said imaging computer calculates the standard correction term $\delta p_{cor}$ using the equation:

$$\delta p_{cor} = -\ln(1 - S_{cor}/P_s),$$

wherein $P_s$ is the normalized total intensity distribution including scatter radiation.

23. A radiographic system according to claim 21 wherein said imaging computer calculates the standard correction term $\delta p_{cor}$ using the equation:

$$\delta p_{cor} = p_{cor} - p_s,$$

wherein $p_{cor} = -\ln(P_s) - \ln(1 - S_{cor}/P_s)$, $p_s$ is the logarithmized total projection data, and $P_s$ is the normalized total intensity distribution including scatter radiation.

24. A radiographic system according to claim 21 wherein said imaging computer estimates the scatter radiation distribution $S_{cor}(y,z)$ based on a measurement thereof.

25. A radiographic system according to claim 21 wherein said imaging computer estimates the scatter radiation distribution $S_{cor}(y,z)$ by calculation thereof.

26. A radiography system comprising:
    an x-ray imaging system comprising an x-ray source that emits a radiation beam onto a flat panel radiation detector, to acquire tomographic data from a subject in a scan having a scatter radiation distribution $S_{cor}(y,z)$ associated therewith, where (y,z) represent the coordinates on the detector; and
    an imaging computer configured to generate an image from the tomographic data and automatically correct scatter radiation errors by estimating said scatter radiation distribution $S_{cor}(y,z)$, automatically calculating a standard correction term $\delta p_{cor}$ based on the estimated scatter radiation distribution $S_{cor}(y,z)$, automatically determining a local noise variance, automatically determining a local noise growth term, and when said growth term reaches a predetermines size automatically implementing an adaptive noise correction by adaptively determining a local noise filter mask size, adaptively noise filtering the standard correction term $\delta p_{cor}$ with $\phi(\delta p_{cor})$, and adding the noise-filtered standard correction term $\phi(\delta p_{cor})$ to the logarithmized, measured total projection data $p_s$, and automatically implementing a non-adaptive noise correction when the noise growth term has not reached said predetermined size, by noise filtering the standard correction term $\delta p_{cor}$ with $F(\delta p_{cor})$, and adding the noise-filtered standard correction term $F(\delta p_{cor})$ to the logarithmized, measured total projection data $p_s$.

27. A radiography system according to claim 26 wherein said imaging computer calculates the noise growth term with the equation $$(S/P)*\sigma(p_s)*\sqrt{I_0},$$

wherein S is the normalized scatter radiation distribution, P is the normalized primary radiation distribution, $\sigma(p_s)$ is the interference ratio due to scatter radiation and $I_0$ is the unattenuated intensity distribution without a subject in the beam path of radiation in which said flat panel is disposed.

28. A radiography system according to claim 26 wherein said imaging computer calculates the noise growth term with the equation $$\sqrt{e^{p_s}}\,\frac{S_{cor}}{P_{cor}},$$

wherein $S_{cor}$ is the estimated scatter radiation used for the correction, $P_{cor}$ is the estimated primary intensity distribution corrected with $S_{cor}$, and $P_s$ is the total intensity distribution.

29. A radiographic system according to claim 26 wherein said imaging computer calculates the standard correction term $\delta p_{cor}$ using the equation:

$$\delta p_{cor} = -\ln(1 - S_{cor}/P_s),$$

wherein $P_s$ is the normalized total intensity distribution including scatter radiation.

30. A radiographic system according to claim 26 wherein said imaging computer calculates the standard correction term $\delta p_{cor}$ using the equation:

$$\delta p_{cor} = p_{cor} - p_s,$$

wherein $p_{cor} = -\ln(P_s) - \ln(1 - S_{cor}/P_s)$, $p_s$ is the logarithmized total projection data, and $P_s$ is the normalized total intensity distribution including scatter radiation.

31. A radiographic system according to claim 26 wherein said imaging computer estimates the scatter radiation distribution $S_{cor}(y,z)$ based on a measurement thereof.

32. A radiographic system according to claim 26 wherein said imaging computer estimates the scatter radiation distribution $S_{cor}(y,z)$ by calculation thereof.

33. A radiography system comprising:

an x-ray imaging system comprising an x-ray source that emits a radiation beam onto a flat panel radiation detector, to acquire tomographic data from a subject in a scan having a scatter radiation distribution $S_{cor}(y,z)$ associated therewith, where (y,z) represent the coordinates on the detector; and an imaging computer configured to generate an image from the tomographic data and automatically correct scatter radiation errors by estimating said scatter radiation distribution $S_{cor}(y,z)$, automatically calculating a standard correction term $\delta p_{cor}$ cor based on the estimated scatter radiation distribution $S_{cor}(y,z)$, automatically segmenting an uncorrected projection image, automatically determining a local noise variance, automatically implementing a segment-dependent determination of a local noise filter mask size, automatically implementing segment-dependent noise filtering of the standard correction term $\delta p_{cor}$ with $(\delta p_{cor})$, and automatically adding the noise-filtered correction term $\phi(\delta p_{cor})$ to the logarithmized, measured total projection data $p_s$.

34. A radiography system according to claim 33 wherein said imaging computer implements said segment-dependent noise filtering at least partially as an adaptive noise variance-dependent noise filtering.

35. A radiographic system according to claim 33 wherein said imaging computer calculates the standard correction term $\delta p_{cor}$ using the equation:

$$\delta p_{cor} = -\ln(1 - S_{cor}/P_s),$$

wherein $P_s$ is the normalized total intensity distribution including scatter radiation.

36. A radiographic system according to claim 33 wherein said imaging computer calculates the standard correction term $\delta p_{cor}$ using the equation:

$$\delta p_{cor} = p_{cor} - p_s,$$

wherein $p_{cor} = -\ln(P_s) - \ln(1 - S_{cor}/P_s)$, $p_s$ is the logarithmized total projection data, and $P_s$ is the normalized total intensity distribution including scatter radiation.

37. A radiographic system according to claim 33 wherein said imaging computer estimates the scatter radiation distribution $S_{cor}(y,z)$ based on a measurement thereof.

38. A radiographic system according to claim 33 wherein said imaging computer estimates the scatter radiation distribution $S_{cor}(y,z)$ by calculation thereof.

\* \* \* \* \*